United States Patent [19]

Patton et al.

[11] Patent Number: 4,992,564

[45] Date of Patent: *Feb. 12, 1991

[54] PREPARATION OF 6-SUBSTITUTED 4-CHROMANONES

[75] Inventors: Jerry R. Patton; Narayanasamy Gurusamy, both of Ballwin, Mo.

[73] Assignee: Mallinckrodt, Inc., St. Louis, Mo.

[*] Notice: The portion of the term of this patent subsequent to Apr. 17, 2007 has been disclaimed.

[21] Appl. No.: 401,188

[22] Filed: Aug. 31, 1989

Related U.S. Application Data

[63] Continuation of Ser. No. 151,938, Feb. 3, 1988, Pat. No. 4,918,203.

[51] Int. Cl.$^5$ ............... C07D 311/22; C07D 311/38; C07D 335/06
[52] U.S. Cl. ............................. 549/401; 549/403; 549/23
[58] Field of Search ................. 549/401, 403, 23

[56] References Cited

PUBLICATIONS

Offe et al., Chem. Ber., 80, pp. 458–463, 464–469, (1947).
Amakasu et al., J. Org. Chem., 31, pp. 1433–1436, (1966).
Dann et al., Ann. Chem., 587, pp. 16–34, (1954).
Tilak et al., Tetrahedron, 24, pp. 949–957, (1968).
Ellis, "Chromenes, Chromenones and Chromones", John Wiley & Sons, New York, N.Y., 1977, pp. 228–235.

*Primary Examiner*—Nicky Chan
*Attorney, Agent, or Firm*—Bernard, Rothwell & Brown

[57] ABSTRACT

Disclosed is a practical and efficient process for preparing 6-substituted 4-chromanones from phenolic acrylate ester compounds derivable from para-substituted phenolic or thiophenolic compounds and beta-unsubstituted acrylic acid compounds which are esterifiable therewith. The process includes effecting rearrangement of a phenolic or thiophenolic acrylate ester in the presence of a rearrangement effective amount of hydrogen fluoride to the corresponding hydroxy—or mercapto (vinyl ketone) wherein the carbonyl carbon atom of the vinyl carboxy group is directly attached to the benzene ring ortho to the hydroxy or mercapto group. Thereafter, the vinyl ketone is cyclized to the corresponding 6-substituted 4-chromanone in the presence of a cyclization-effective amount of hydrogen fluoride. The 6-substituted 4-chromanones prepared by the process are useful as intermediates for preparing pharmaceutical agents.

4 Claims, No Drawings

PREPARATION OF 6-SUBSTITUTED 4-CHROMANONES

This application is a continuation of application Ser. No. 151,938, filed Feb. 3, 1988, now U.S. Pat. No. 4,918,203.

BACKGROUND OF THE INVENTION

This invention relates to a process for preparing 6-substituted 4-chromanones from phenolic acrylate ester compounds derivable from para-substituted phenolic compounds and beta-unsubstituted acrylic acid compounds which are esterifiable therewith. The 6-substituted 4-chromanones prepared by the process of this invention are useful as intermediates for preparing pharmaceutical agents.

Preparation of 4-chromanones via condensation of beta-substituted, beta,beta-disubstituted and alpha, beta-disubstituted acrylic acids with phenolic compounds in anhydrous hydrogen fluoride is disclosed by Offe and Barkow in Chem. Ber. 80, 458 (1947), hereinafter Offe I. However, Offe I does not disclose such preparation using beta-unsubstituted acrylic acids. Offe and Barkow indicate in Chem. Ber. 80, 464 (1947), hereinafter Offe II, that it is possible but not practical to prepare 4-chromanones in hydrogen fluoride from phenol and beta-unsubstituted acrylic acid compounds such as acrylic acid per se. Offe II does not disclose how such preparation is possible. Similarly, Amakasu and Sato indicate in J. Org. Chem. 31, 1433 (1966) that 4-chromanones are not obtainable via reaction of acrylic acid or alpha-monosubstituted acrylic acid with phenols.

DESCRIPTION OF THE INVENTION

It has now been found unexpectedly that 6-substituted 4-chromanones more particularly defined hereinbelow can be prepared in practical and efficient manner from phenolic acrylate esters of para-substituted phenolic compounds and beta-unsubstituted acrylic acid compounds in the presence of hydrogen fluoride. The beta-unsubstituted acrylic acid compounds include acrylic acid per se and alpha-monosubstituted acrylic acid. It has also been found that the esters can be prepared in practical and efficient manner by condensing the phenolic compounds with the acrylic acid compounds in the presence of hydrogen fluoride in an initially anhydrous system. Isolation of the various intermediate compounds is not required, thereby advantageously permitting preparation of the 6-substituted chromanones from the phenolic compounds and acrylic acid compounds by an integral overall process in a single reaction mixture and a single reaction vessel.

Generally stated, the present invention provides a process for preparing a 6-substituted-4-chromanone having the formula

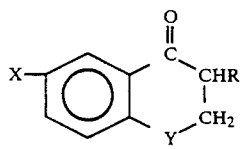
(1)

where

X is a member selected from the group consisting of halogen atoms, nitro, amino and alkyl having from 1 to about 20 carbon atoms;

Y is an oxygen or sulfur atom; and

R is a member selected from the group consisting of a hydrogen atom, halogen atoms, alkyl having from 1 to about 20 carbon atoms and aryl having from 6 to about 12 carbons; which comprises (a) effecting rearrangement of a phenolic acrylate ester of a phenol or thiophenol, said ester having the formula

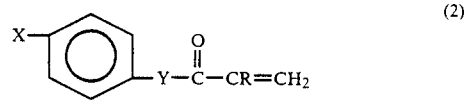
(2)

where X, Y and R are as defined above, to a hydroxy- or mercapto-(vinyl ketone) having the formula

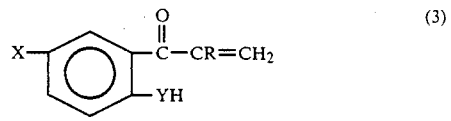
(3)

where X, Y and R are as defined above, in the presence of a Fries rearrangement-effecting amount of hydrogen fluoride under Fries rearrangement conditions comprising a substantially anhydrous liquid reaction mixture initially comprising said phenolic acrylate ester and hydrogen fluoride; and (b) effecting cyclization of said ketone in the presence of a cyclizing amount of hydrogen fluoride under cyclization conditions to form the 6-substituted-4-chromanone, said cyclization conditions comprising a substantially anhydrous liquid reaction mixture initially comprising said ketone and hydrogen fluoride.

In another aspect, generally stated, the above-described process of this invention further comprises preparing said phenolic acrylate ester by contacting a para-substituted phenolic compound having the formula $$p-X-C_6H_4-Y-Z \quad (4)$$

where

X is a member selected from the group consisting of halogen atoms, nitro, amino and alkyl having from 1 to about 20 carbon atoms;

Y is an oxygen or sulfur atom; and

Z is a member selected from the group consisting of hydrogen atom, alkyl having from 1 to 20 carbon atoms and aryl having from 6 to about 12 carbon atoms, with a beta-unsubstituted acrylic acid compound having the formula $$CH_2=CR-C(=O)OH \quad (5)$$

where R is a member selected from the group consisting of a hydrogen atom, halogen atoms, alkyl having from 1 to about 20 carbon atoms and aryl having from 6 to about 12 carbons, in the presence of a condensation-effecting amount of hydrogen fluoride under ester-forming condensation conditions to form said phenolic acrylate ester, said condensation conditions comprising a substantially anhydrous liquid reaction mixture of said para-substituted phenolic compound, said beta-unsubstituted acrylic acid compound and hydrogen fluoride.

DETAILED DESCRIPTION OF THE INVENTION AND THE MANNER AND PROCESS OF CARRYING IT OUT

The phenolic acrylate ester of formula (2) above can be prepared in any suitable manner, including by well known methods such as transesterification of a phenolic ester containing the p—X—$C_6H_4$—Y— moiety of formula (2) and an acid moiety having its carbonyl carbon bonded directly to the Y atom with the beta-unsubstituted acrylic acid compound of formula (5) above in the presence of a mineral acid. Another well known method is esterification of a phenolic compound of formula (4) above where Z is H with an acrylol chloride which is an acid chloride of an acid of formula (5).

Preferably, however, the ester of formula (2) is prepared by contacting a para-substituted phenolic compound of formula (4) above with a beta-unsubstituted acrylic acid compound of formula (5) above. Such contacting is effected in the presence of a condensation-effecting amount of hydrogen fluoride under ester-forming condensation conditions, including an initially substantially anhydrous liquid reaction mixture of the phenolic compound, the acrylic acid compound and hydrogen fluoride.

As used herein, the term "substantially anhydrous" means that the substance referred to does not contain more than 5% water by weight, preferably not more than 1% water.

The ester-forming reaction can be carried out at any suitable temperature, provided that the reaction mixture is under sufficient pressure to keep the para-substitutd phenolic compound, the acrylic acid compound, the hydrogen fluoride, the ester and any other reaction mixture components which may be employed in the liquid state. In general, the temperature may be, for example, from about 0° C. to about 150° C., preferably from about 20° C. to about 50° C., and more preferably from about 40° C. to about 50° C. In general, the reaction pressure may be, for example, from about 0 to about 300 psig, preferably from about 0 to about 150 psig, and more preferably not more than 100 psig. The reaction can be carried out in any reaction vessel suitable for holding hydrogen fluoride and the other components of the reaction mixture. The reaction vessel is preferably a closed vessel equipped with means for stirring the reaction mixture, means for measuring the temperature of the mixture and means for controlling such temperature. Although the components of the reaction mixture may be added in any order, preferably the para-substituted phenolic compound and acrylic acid compound are admixed and thereafter the hydrogen fluoride is added to the resulting admixture with stirring.

The acrylic acid compound and the para-substituted phenolic compound may be added in stoichiometric amounts (i.e. in 1:1 mole ratio). Advantageously, the acrylic acid is added in excess of the stoichiometric amount, thereby tending to effect complete reaction of the phenolic compound. The mole ratio of the acrylic acid compound to the phenolic compound may be, for example, from about 1:1 to about 2:1, preferably from about 1.05:1 to about 1.5:1, and more preferably about 1.5:1.

Hydrogen fluoride is added in any condensation-effective amount and may be added in an amount, for example, from about 5 to about 50 moles, preferably from about 10 to about 20 moles, and more preferably about 15 moles, per mole of the phenolic compound added. The time required for carrying out the ester-forming reaction depends on the particular compounds and reaction conditions employed. In general, the reaction can be carried to completion within one hour and in may instances within 0.5 hour.

The ester-forming reaction is preferably carried out in the additional presence of any agent for inhibiting polymerization of the acrylic acid and the ester being prepared. Suitable polymerization-inhibiting agents include hydroquinone, sulfur, phenothiazine (preferred), compatible mixtures thereof and the like. The inhibitor can be included in any suitable amount effective for inhibiting polymerization of the acrylic acid compound and the ester being formed, such as, for example, from about 0.01 to about 0.1 mole per 100 moles of the acrylic acid compound added. On the same basis, approximately 0.1 mole of phenothiazine is preferred.

Water adversely interferes with the ester-forming reaction. For best results, the initial reaction mixture is free of water. Hydrogen fluoride serves to catalyze the reaction and tie up the water formed during the course of the ester-forming reaction.

Whether the phenolic acrylate ester is prepared by the ester-forming process of this invention or is otherwise provided, the ester is next converted to the chromanone of formula (1) above. Such conversion is carried out by first converting the ester to the hydroxy- or mercapto-(vinyl ketone) of formula (3) above and thereafter converting the ketone to the 6-substituted 4-chromanone of formula (1) above.

The first conversion, i.e. rearrangement of a phenolic acrylate ester of formula (2) above to a ketone of formula (3) above, is effected in the presence of a Fries rearrangement-effective amount of hydrogen fluoride under Fries rearrangement conditions, preferably in a substantially anhydrous liquid reaction mixture initially comprising the phenolic acrylate ester compound and hydrogen fluoride. Although a substantially anhydrous reaction mixture is not required for the rearrangement reaction, generally better yields result therefrom.

The ester-to-ketone rearrangement reaction can be carried out at any suitable temperature, provided that the reaction mixture is under sufficient pressure to keep the reaction mixture components in the liquid state. In general, the temperature may be, for example, from about 0° C. to about 150° C., preferably from about 100° C. to about 120° C., and more preferably about 100° C. In general, the reaction pressure may be, for example, from about 50 to about 250 psig, preferably from about 100 to about 150 psig, and more preferably about 140 psig. The reaction can be carried out in any reaction vessel suitable for holding hydrogen fluoride and the balance of the reaction mixture. The reaction vessel is preferably a closed vessel equipped with means for stirring the reaction mixture, means for stirring the reaction mixture, means for measuring the temperature of the mixture and means for controlling such temperature. Where the ester is not prepared in hydrogen fluoride, the components of the rearrangement reaction mixture may be added in any order, bu preferably the hydrogen fluoride is added to the ester with stirring. Advantageously and preferably, the ester is prepared in the presence of hydrogen fluoride as herein taught and rearrangement to the ketone is effected in the reaction mixture employed in the ester-preparation step without isolating the resulting ester.

Hydrogen fluoride is employed in any rearrangement-effective amount and may be present in an amount, for example, from about 5 to about 50 moles, preferably from about 10 to about 20 moles, and more preferably about 15 moles, per mole of the ester. The time required for carrying out the ester-to-ketone rearrangement reaction depends on the particular ester being rearranged and reaction conditions employed. In general, the reaction can be carried to completion within two hours and in many instances within about 0.1 to 0.5 hour.

The acrylate ester-rearrangement reaction is preferably carried out in the additional presence of an agent for inhibiting polymerization of the ester (and the vinyl ketone being prepared). Suitable polymerization-inhibiting agents include hydroquinone, sulfur, phenothiazine (preferred), compatible mixtures thereof and the like. The inhibitor can be included in any suitable amount effective for inhibiting polymerization of the acrylate ester compound and the ketone being prepared, such as, for example, from about 0.01 to about 0.1 mole per 100 moles of the acrylate ester compound employed. On the same basis, approximately 0.1 mole of phenothiazine is preferred.

Those skilled in the art will appreciate that, as shown by formula (3) above, in the ketone the carbonyl carbon atom of the vinyl carboxy group is directly attached to the benzene ring ortho to the hydroxy or mercapto group represented by —YH in such formula. Rearrangement to such ketone rather than rearrangement to a structure wherein such carbonyl carbon atom is attached meta to the —YH group is critical for preparing 6-substituted 4-chromanones. It is also critical that the X substituent be para to the —YH group. If the X substituent were ortho or meta to the —YH group, the ester would rearrange to a structure wherein the vinyl carboxy group is attached para to the —YH group. Such structure would be inoperable for cyclization to a chromanone structure. Moreover, if X were ortho to the —YH group, only one of the two ortho positions would be available for displacement of a hydrogen atom in the ester by the vinyl carboxy group to from a 4-chromanone-precursor ketone.

After rearrangement of the ester to the ketone of formula (3), the ketone is cyclized to the corresponding 6-substituted 4-chromanone. Cyclization is effected in the presence of a cyclization-effective amount of hydrogen fluoride under cyclization conditions, preferably in a substantially anhydrous liquid reaction mixture initially comprising the ketone and hydrogen fluoride. Although a substantially anhydrous reaction mixture is not required for the cyclization reaction, generally better yields result therefrom.

The cyclization reaction can be carried out at any suitable temperature, provided that the reaction mixture is under sufficient pressure to keep the reaction mixture components in the liquid state. In general, the temperature may be, for example, from about 100° C. to about 200° C., preferably from about 100° C. to about 120° C., and more preferably about 100° C. In general, the reaction pressure may be, for example, from about 50 to bout 250 psig, preferably from about 100 to about 150 psig, and more preferably about 140 psig. The reaction can be carried out in any reaction vessel suitable for holding hydrogen fluoride and the balance of the reaction mixture. The reaction vessel is preferably a closed vessel equipped with means for stirring the reaction mixture, means for measuring the temperature of the mixture and means for controlling such temperature. When the ketone is not cyclized in the reaction mixture in which it was prepared, the components of the cyclization reaction mixture may be added in any order, but preferably the hydrogen fluoride is added to the ketone with stirring. Advantageously and preferably, cyclization of the ketone is effected in the reaction mixture employed in the ester-to-ketone rearrangement step without isolating the resulting ketone.

Hydrogen fluoride is employed in any cyclization-effective amount and may be present in an amount, for example, from about 5 to about 50 moles, preferably from about 10 to about 20 moles, and more preferably about 15 moles, per mole of the ketone. The time required for carrying out the cyclization reaction depends on the particular ketone being cyclized and reaction conditions employed. In general, the reaction can be carried to completion within one hour.

The ketone-cyclization reaction is preferably carried out in the additional presence of an agent for inhibiting polymerization of the vinyl ketone. Suitable polymerization-inhibiting agents include hydroquinone, sulfur, phenothiazine (preferred), compatible mixtures thereof and the like. The inhibitor can be included in any suitable amount effective for inhibiting polymerization of the vinyl ketone, such as, for example, from about 0.01 to about 0.1 mole per 100 moles of the vinyl ketone employed. On the same basis, approximately 0.1 mole of phenothiazine is preferred.

The overall time for effecting rearrangement and cyclization is generally 3 to 6 hours.

After the cyclization reaction is complete, hydrogen fluoride can be recovered, if desired, by distillation of at least a portion thereof from the reaction mixture. With or without prior removal of hydrogen fluoride, the reaction mixture may be admixed with water to precipitate the 6-substituted 4-chromanone, which then may be washed and dried if desired. Preferably, cold water, e.g. from 0° C. to 20° C. (preferably 0° C. to 5° C.) is admixed with the reaction mixture.

Illustrative of the 6-substituted 4-chromanones included within formula (1) above are:
 (a) 6-fluoro-4-chromanone,
 (b) 6-chloro-4-chromanone,
 (c) 6-bromo-4-chromanone,
 (d) 6-methyl-4-chromanone,
 (e) 6-nitro-4-chromanone,
 (f) 6-amino-4-chromanone,
 (g) the 6-substituted 3-methyl-4-chromanones corresponding the above compounds (a) through (f),
 (h) the 6-substituted 3-halo-4-chromanones corresponding to the above compounds (a) through (f), and
 (i) the 6-substituted thio-4-chromanones corresponding to the above compounds (a) through (h).

Illustrative of the corresponding para-substituted phenolic compounds included within formula (4) above and from which the above illustrative 6-substituted 4-chromanones may be prepared are:
 (a') p-fluorophenol,
 (b') p-chlorophenol,
 (c') p-bromophenol,
 (d') p-methylphenol (i.e. p-cresol),
 (e') p-nitrophenol, (f') p-aminophenol,
(g') same as compounds (a') through (f'),
(h') see (g'), and
(i') the p-thiophenols corresponding to the above compounds (a') through (h').

Illustrative of the corresponding beta-unsubstituted acrylic acid compounds included within formula (5) above and from which the above illustrative 6-substituted 4-chromanones may be prepared are:

(a'') acrylic acid for the above compounds (a) through (f) and their corresponding thio compounds
(b'') methacrylic acid for the above compounds (g) and their corresponding thio compounds, and
(c'') 2-halo-acrylic acid for the above compounds (h) and their corresponding thio compounds.

Although there is no known limit on the halogens which may be employed as R and X in the above formulas, fluorine, chlorine, bromine and iodine atoms are generally preferred, and more preferably F, Cl and Br.

Generally preferred alkyl and aryl groups from which R and Z in the above formulas can be selected are methyl, ethyl and phenyl.

Practice of the present invention is illustrated by the following non-limiting examples. All parts, percents and other amounts throughout this disclosure are by weight unless otherwise indicated.

In the examples which follow, all products were characterized as 4-Chromanones by melting point, HPLC, infrared analysis and NMR.

EXAMPLE 1

Preparation of 6-Fluoro-4-Chromanone

A 400 ml stainless steel Parr reactor was charged with para-fluorophenol (28.4 grams), acrylic acid (28.8 grams), and an inhibitor phenothiazine (0.02 grams). The system was sealed, evacuated and cooled in dry ice/acetone before the anhydrous hydrogen fluoride (117 grams) was condensed into the system. The mixture was then warmed to 40° C. for one hour thirty minutes with stirring before being heated to 100° C. for four hours thirty minutes. The excess HF was them removed and the system cooled to 0° C. and opened to give 62 grams of brown oil which was washed with D.I. water to give 50 grams of material to be extracted. The 6-Fluoro-4-Chromanone was collected and recrystallized from methanol/water. The HPLC yield was 75%, isolated 52%.

EXAMPLE 2

Preparation of 6-Fluoro-4-Chromanone

A 400 ml stainless steel Parr reactor was charged with previously prepared p-fluorophenylacrylate (41.5 grams) and phenothiazine (0.02 grams) before being sealed and evacuated. The system was cooled in dry ice/acetone and anhydrous hydrogen fluoride (40 grams) was vacuum transferred into the reactor. The mixture was heated to 100° C. for four hours before the hydrogen fluoride was vented and the system cooled to 0° C. The reactor was opened and worked up as in Example 1 to give the desired 6-Fluoro-4-Chromanone.

EXAMPLE 3

Preparation of 6-Nitro-4-Chromanone

Following the same procedure as Example 1, p-nitrophenol (34.8 grams), acrylic acid (27 grams), and an inhibitor, phenothiazine (0.02 grams) was added to the pressure reactor. The anhydrous hydrogen fluoride (110 grams) was added before the system was warmed. When the reaction temperature was attained, a pressure of 140 psig was noted, similar to previous reactions. Work-up was carried out as previous examples and the 6-Nitro-4-Chromanone was isolated and characterized.

EXAMPLE 4

Preparation of 6-Bromo-4-Chromanone

Following the procedure of Example 1, para-bromophenol (43.25 grams), acrylic acid (27 grams) and phenothiazine (0.02 grams) were added to the pressure reactor. The system was closed and evacuated before being cooled to −78° C. and the anhydrous hydrogen fluoride (110 grams) was added. After the mixture was heated and stirred for six hours at 100° C., 140 psig, the excess hydrogen fluoride was vented and the reaction mixture cooled to 0°–5° C. After washing the mixture with D.I. water, HPLC analysis indicated one major product which was separated and characterized as 6-Bromo-4-Chromanone.

EXAMPLE 5

Preparation of 6-Fluoro-3-Methyl-4-Chromanone

Using the procedure established in Example 1, the Parr reactor was charged with para-fluorophenol (28 grams), methacrylic acid (32 grams), and phenothiazine (0.02 grams). The system was sealed, evacuated, and cooled to −78° C. before the anhydrous HF (110 grams) was vacuum transferred to the reactor. The mixture was warmed to 40° C. for one hour then up to 100° C. for five hours. The pressure was recorded at 160 psig at the reaction temperature. The excess hydrogen fluoride was vented and the mixture cooled to 5° C. before being washed with D.I. water. Analysis by HPLC indicated one major product which was isolated and characterized to be 6-Fluoro-3-Methyl-4-Chromanone. The presence of a minor amount (not more than 5%) of residual hydroxy vinyl ketone corresponding to 6-fluoro-3-methyl-4-chromanone was evidenced by IR and HPLC analysis taken with the starting materials and preparation procedure.

EXAMPLE 6

Preparation of 6-Fluoro-thio-4-Chromanone

The 400 ml Parr pressure reactor was charged with para-fluorothiophenol (19.2 grams), acrylic acid (16.2 grams), and phenothiazine (0.02 gram). The reactor was closed, evacuated and cooled to −78° C. before the anhydrous hydrogen fluoride (70 grams) was added. The mixture was warmed to 40° C. for one hour then heated to 100° C. for 4.5 hours. After the reaction time had been reached, the excess hydrogen fluoride was vented and the product washed with D.I. water. Analysis by HPLC indicated the desired product, 6-Fluoro-thio-4-Chromanone to be present. Work-up gave the product which was characterized by infrared and NMR analysis.

EXAMPLE 7

Preparation of 6-Fluoro-4-Chromanone

Using the procedure established in Example 1, the reactor was charged with p-fluoroanisole (31.5 grams), acrylic acid (27 grams) and phenothiazine (0.02 grams) before being sealed, evacuated, and cooled to −78° C. The anhydrous hydrogen fluoride (110 grams) was vacuum transferred into the reactor and the mixture warmed to 40° C. for one hour then 100° C. for 4.5 hours. The excess hydrogen fluoride was then vented and the reactor cooled to 5° C. before being opened and the contents washed with D.I. water. Analysis by HPLC indicated the presence of para-fluoroanisole and 6-Fluoro-4-Chromanone. The para-fluoroanisole was removed by distillation and the desired 6-Fluoro-4-Chromanone isolated by extraction and characterized.

EXAMPLE 8

Attempted Preparation of 7-Fluoro-4-Chromanone

Following the same procedure established in Example 1, the reactor was charged with meta-fluorophenol (28 grams), acrylic acid (27 grams), and phenothiazine (0.02 grams). The reactor was sealed, evacuated and cooled to −78° C. before the anhydrous hydrogen fluoride (125 grams) was added. The mixture was stirred and warmed to 40° C. for one hour then to 100° C. for 4.5 hours as the pressure was recorded at 140 psig. After venting the excess hydrogen fluoride the reactor was cooled to 5° C. and the mixture washed with D.I. water. Analysis by HPLC indicated no 4-Chromanones to be present. A mixture of by-products were seen.

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. A process for preparing a 6-substituted 4-chromanone having the formula

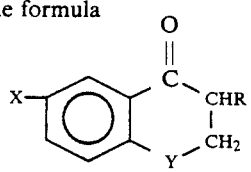

where

X is a member selected from the group consisting of halogen atoms, nitro, amino and alkyl having from 1 to about 20 carbon atoms;

Y is an oxygen or sulfur atom; and

R is a member selected from the group consisting of a hydrogen atom, halogen atom, alkyl having from 1 to about 20 carbon atoms and aryl having from about 6 to about 12 carbons; which comprises (a) effecting rearrangement of a phenolic acrylate ester of a phenol or thiophenol, said ester having the formula

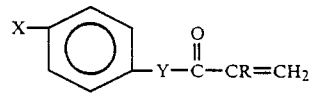

where X, Y and R are as defined above, to a hydroxy- or mercapto-(vinyl ketone) having the formula

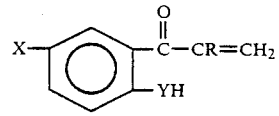

where X, Y and R are as defined above, in the presence of a Fries rearrangement-effecting amount of hydrogen fluoride under Fries rearrangement conditions comprising a substantially anhydrous liquid reaction mixture initially comprising said phenolic acrylate ester and hydrogen fluoride; and (b) effecting cyclization of said ketone in the presence of a cyclizing amount of hydrogen fluoride under cyclization conditions to form the 6-substituted 4-chromanone, said cyclization conditions comprising a substantially anhydrous liquid reaction mixture initially comprising said ketone and hydrogen fluoride.

2. The process of claim 1 wherein the cyclization step is effected in the reaction mixture employed in the rearrangement step without isolating said ketone.

3. The process of claim 1, wherein the rearrangement and cyclization steps are effected in the presence of a polymerization-inhibiting amount of an agent for inhibiting polymerization of said ester and said ketone.

4. The process of claim 1 wherein said ester is para-fluorophenylacrylate and said 6-substituted-4-chromanone is 6-fluoro-4-chromanone.

* * * * *

UNITED STATES PATENT AND TRADEMARK OFFICE
CERTIFICATE OF CORRECTION

PATENT NO. : 4,992,564

DATED : February 12, 1991

INVENTOR(S) : Patton et al.

It is certified that error appears in the above-identified patent and that said Letters Patent is hereby corrected as shown below:

Column 2, line 54, insert --about-- between "to" and "20"

Column 5, line 66, "bout" should be --about--

Column 6, line 6, "When" should be --Where--

Column 7, line 42, "them" should be --then--

Column 8, line 42, "analysis" should be --analyses--

Signed and Sealed this

Fifteenth Day of December, 1992

*Attest:*

DOUGLAS B. COMER

*Attesting Officer*     *Acting Commissioner of Patents and Trademarks*